(12) United States Patent
Pandelidis et al.

(10) Patent No.: US 8,888,841 B2
(45) Date of Patent: Nov. 18, 2014

(54) BIOABSORBABLE IMPLANTS

(75) Inventors: Ioannis Pandelidis, Sharon, MA (US); Mark Steckel, Zollikerberg (CH)

(73) Assignee: Zorion Medical, Inc., Zionsville, IN (US)

(*) Notice: Subject to any disclaimer, the term of this patent is extended or adjusted under 35 U.S.C. 154(b) by 146 days.

(21) Appl. No.: 13/165,247

(22) Filed: Jun. 21, 2011

(65) Prior Publication Data

US 2011/0319977 A1 Dec. 29, 2011

Related U.S. Application Data

(60) Provisional application No. 61/398,030, filed on Jun. 21, 2010, provisional application No. 61/399,340, filed on Jul. 12, 2010, provisional application No. 61/458,705, filed on Dec. 1, 2010.

(51) Int. Cl.

| | | |
|---|---|---|
| A61F 2/06 | (2013.01) | |
| A61L 31/14 | (2006.01) | |
| A61L 31/16 | (2006.01) | |
| C22C 1/00 | (2006.01) | |
| A61L 27/54 | (2006.01) | |
| A61L 27/04 | (2006.01) | |
| A61L 31/02 | (2006.01) | |
| A61L 31/18 | (2006.01) | |
| C22C 23/00 | (2006.01) | |
| C22F 1/06 | (2006.01) | |
| A61L 27/58 | (2006.01) | |
| A61F 2/89 | (2013.01) | |
| A61F 2/82 | (2013.01) | |

(52) U.S. Cl.
CPC ............ *A61L 27/047* (2013.01); *A61L 31/148* (2013.01); *A61L 31/16* (2013.01); *C22C 1/00* (2013.01); *A61F 2/89* (2013.01); *A61L 27/54* (2013.01); *A61F 2210/0004* (2013.01); *A61L 31/022* (2013.01); *A61L 31/18* (2013.01); *A61F 2250/0071* (2013.01); *A61F 2002/828* (2013.01); *C22C 23/00* (2013.01); *C22F 1/06* (2013.01); *A61L 27/58* (2013.01)
USPC .......... 623/1.42; 623/1.34; 623/1.38; 623/1.15

(58) Field of Classification Search
None
See application file for complete search history.

(56) References Cited

U.S. PATENT DOCUMENTS

| | | | |
|---|---|---|---|
| 5,370,683 | A | 12/1994 | Fontaine |
| 6,287,332 | B1 | 9/2001 | Bolz et al. |

(Continued)

FOREIGN PATENT DOCUMENTS

| | | |
|---|---|---|
| CN | 101214396 A | 7/2008 |
| CN | 101249286 A | 8/2008 |

(Continued)

OTHER PUBLICATIONS

International Search Report and Written Opinion, Application No. PCT/US2011/041258, dated Jan. 31, 2012, 17 pages.

(Continued)

*Primary Examiner* — Thomas J Sweet
*Assistant Examiner* — Tiffany Shipmon
(74) *Attorney, Agent, or Firm* — Taft Stettinius & Hollister LLP; Ryan O. White

(57) ABSTRACT

A bioabsorbable implant including an elongated metallic element including more than 50% a metal substantially free of rare earth metals, with the elongated metallic element defining at least a portion of the bioabsorbable implant.

17 Claims, 12 Drawing Sheets

(56) References Cited

U.S. PATENT DOCUMENTS

| | | | |
|---|---|---|---|
| 6,585,755 B2 | 7/2003 | Jackson et al. | |
| 6,602,282 B1 | 8/2003 | Yan | |
| 6,629,994 B2 | 10/2003 | Gomez et al. | |
| 6,652,579 B1 | 11/2003 | Cox et al. | |
| 6,713,119 B2 | 3/2004 | Hossainy et al. | |
| 6,730,116 B1 | 5/2004 | Wolinsky et al. | |
| 6,776,793 B2 | 8/2004 | Brown et al. | |
| 7,004,968 B2 | 2/2006 | Lootz et al. | |
| 7,018,401 B1 | 3/2006 | Hyodoh et al. | |
| 7,070,607 B2 | 7/2006 | Murayama et al. | |
| 7,083,640 B2 | 8/2006 | Lombardi et al. | |
| 7,192,443 B2 | 3/2007 | Solem et al. | |
| 7,674,416 B2 | 3/2010 | Hong et al. | |
| 7,727,272 B2 | 6/2010 | Schlun et al. | |
| 7,736,687 B2 | 6/2010 | Sims et al. | |
| 7,806,916 B2 | 10/2010 | Delaloye et al. | |
| 7,809,447 B2 | 10/2010 | Dreier et al. | |
| 7,833,260 B2 | 11/2010 | Cottone et al. | |
| 7,862,606 B2 | 1/2011 | Lootz et al. | |
| 7,862,607 B2 | 1/2011 | McDermott et al. | |
| 7,913,371 B2 | 3/2011 | Klocke et al. | |
| 7,939,146 B2 | 5/2011 | Borck et al. | |
| 2002/0174922 A1* | 11/2002 | Ishii et al. | 148/671 |
| 2003/0130718 A1 | 7/2003 | Palmas et al. | |
| 2004/0034409 A1 | 2/2004 | Heublein et al. | |
| 2004/0073297 A1 | 4/2004 | Rohde et al. | |
| 2004/0098108 A1 | 5/2004 | Harder et al. | |
| 2004/0172123 A1 | 9/2004 | Lootz et al. | |
| 2005/0027350 A1 | 2/2005 | Momma et al. | |
| 2005/0096722 A1 | 5/2005 | Lootz et al. | |
| 2005/0125051 A1 | 6/2005 | Eidenschink et al. | |
| 2005/0266041 A1 | 12/2005 | Gerold et al. | |
| 2005/0276718 A1 | 12/2005 | Burgermeister et al. | |
| 2006/0018954 A1 | 1/2006 | Kuttler | |
| 2006/0020289 A1 | 1/2006 | Kuttler | |
| 2006/0020315 A1 | 1/2006 | Geistert et al. | |
| 2006/0020317 A1 | 1/2006 | Flach et al. | |
| 2006/0052863 A1 | 3/2006 | Harder et al. | |
| 2006/0052864 A1 | 3/2006 | Harder et al. | |
| 2006/0064160 A1 | 3/2006 | Gerold et al. | |
| 2006/0149352 A1 | 7/2006 | Schlun | |
| 2006/0188486 A1 | 8/2006 | Carpenter et al. | |
| 2006/0212108 A1 | 9/2006 | Tittelbach | |
| 2007/0156231 A1* | 7/2007 | Weber | 623/1.38 |
| 2007/0189915 A1 | 8/2007 | Shrivastava et al. | |
| 2007/0233232 A1 | 10/2007 | St. Germain et al. | |
| 2007/0299512 A1 | 12/2007 | Korzuschnik et al. | |
| 2008/0031765 A1 | 2/2008 | Gerold et al. | |
| 2008/0033530 A1 | 2/2008 | Zberg et al. | |
| 2008/0033531 A1 | 2/2008 | Barthel et al. | |
| 2008/0033533 A1 | 2/2008 | Borck et al. | |
| 2008/0033535 A1 | 2/2008 | Mueller et al. | |
| 2008/0033536 A1 | 2/2008 | Wittchow | |
| 2008/0033537 A1 | 2/2008 | Tittelbach | |
| 2008/0033538 A1 | 2/2008 | Borck et al. | |
| 2008/0033539 A1 | 2/2008 | Sternberg et al. | |
| 2008/0033576 A1 | 2/2008 | Gerold et al. | |
| 2008/0050413 A1 | 2/2008 | Horvers et al. | |
| 2008/0051866 A1 | 2/2008 | Chen et al. | |
| 2008/0051872 A1 | 2/2008 | Borck | |
| 2008/0058923 A1 | 3/2008 | Bertsch et al. | |
| 2008/0097575 A1 | 4/2008 | Cottone | |
| 2008/0103594 A1 | 5/2008 | Loffler et al. | |
| 2008/0131479 A1 | 6/2008 | Weber et al. | |
| 2008/0188927 A1 | 8/2008 | Rohde et al. | |
| 2008/0215140 A1 | 9/2008 | Borck et al. | |
| 2008/0243230 A1 | 10/2008 | Lootz et al. | |
| 2008/0243242 A1 | 10/2008 | Kappelt et al. | |
| 2008/0249608 A1 | 10/2008 | Dave | |
| 2008/0269872 A1 | 10/2008 | Lootz et al. | |
| 2008/0281400 A1 | 11/2008 | Philipp et al. | |
| 2008/0312736 A1 | 12/2008 | Mueller et al. | |
| 2009/0017088 A1 | 1/2009 | Klocke et al. | |
| 2009/0018648 A1 | 1/2009 | Wittchow | |
| 2009/0024210 A1 | 1/2009 | Klocke et al. | |
| 2009/0024211 A1 | 1/2009 | Wittchow | |
| 2009/0030506 A1 | 1/2009 | Klocke et al. | |
| 2009/0030507 A1 | 1/2009 | Klocke et al. | |
| 2009/0048660 A1 | 2/2009 | Adden | |
| 2009/0069884 A1 | 3/2009 | Mueller | |
| 2009/0076596 A1 | 3/2009 | Adden et al. | |
| 2009/0081313 A1* | 3/2009 | Aghion et al. | 424/641 |
| 2009/0110750 A1 | 4/2009 | Greener | |
| 2009/0148496 A1 | 6/2009 | Schmitz et al. | |
| 2009/0164002 A1 | 6/2009 | Becher et al. | |
| 2009/0171452 A1* | 7/2009 | Yamamoto et al. | 623/1.38 |
| 2009/0192594 A1 | 7/2009 | Borck | |
| 2009/0192595 A1 | 7/2009 | Nagura et al. | |
| 2009/0192596 A1 | 7/2009 | Adden | |
| 2009/0198320 A1 | 8/2009 | Mueller et al. | |
| 2009/0204082 A1 | 8/2009 | Wesselmann et al. | |
| 2009/0208555 A1 | 8/2009 | Kuttler et al. | |
| 2009/0228091 A1 | 9/2009 | Surber et al. | |
| 2009/0270979 A1 | 10/2009 | Adden | |
| 2009/0274737 A1 | 11/2009 | Borck | |
| 2009/0292351 A1 | 11/2009 | McClain et al. | |
| 2009/0306725 A1 | 12/2009 | Hiromoto et al. | |
| 2010/0010640 A1 | 1/2010 | Gerold et al. | |
| 2010/0022894 A1 | 1/2010 | Tittelbach et al. | |
| 2010/0023112 A1 | 1/2010 | Borck et al. | |
| 2010/0034899 A1 | 2/2010 | Harder et al. | |
| 2010/0049300 A1 | 2/2010 | Harder | |
| 2010/0076539 A1 | 3/2010 | Klocke et al. | |
| 2010/0076542 A1 | 3/2010 | Orlowski | |
| 2010/0076556 A1 | 3/2010 | Tomantschger et al. | |
| 2010/0082092 A1 | 4/2010 | Gerold | |
| 2010/0087914 A1 | 4/2010 | Bayer et al. | |
| 2010/0087915 A1 | 4/2010 | Bayer et al. | |
| 2010/0087916 A1 | 4/2010 | Bayer et al. | |
| 2010/0106243 A1 | 4/2010 | Wittchow | |
| 2010/0119576 A1 | 5/2010 | Harder et al. | |
| 2010/0119581 A1 | 5/2010 | Gratz et al. | |
| 2010/0121432 A1 | 5/2010 | Klocke et al. | |
| 2010/0131052 A1 | 5/2010 | Kappelt et al. | |
| 2010/0137971 A1 | 6/2010 | Lootz et al. | |
| 2010/0137975 A1 | 6/2010 | Wittchow | |
| 2010/0161030 A1 | 6/2010 | Bayer et al. | |
| 2010/0161053 A1 | 6/2010 | Bayer | |
| 2010/0171492 A1 | 7/2010 | Klocke et al. | |
| 2010/0249900 A1 | 9/2010 | Sager et al. | |
| 2010/0249904 A1 | 9/2010 | Takayuki et al. | |
| 2010/0262221 A1 | 10/2010 | Schafer et al. | |
| 2010/0262229 A1 | 10/2010 | Rohde | |
| 2010/0292639 A1 | 11/2010 | Schwitzer et al. | |
| 2010/0312324 A1 | 12/2010 | Adden et al. | |
| 2010/0324654 A1 | 12/2010 | Bayer et al. | |
| 2010/0324659 A1 | 12/2010 | Mews et al. | |
| 2011/0009952 A1 | 1/2011 | Bayer et al. | |
| 2011/0029064 A1 | 2/2011 | Burpee et al. | |
| 2011/0034991 A1 | 2/2011 | Barthel et al. | |
| 2011/0076319 A1 | 3/2011 | Orlowski et al. | |
| 2011/0077732 A1 | 3/2011 | Bayer et al. | |
| 2011/0093061 A1 | 4/2011 | Lootz et al. | |
| 2011/0112628 A1 | 5/2011 | Bayer | |
| 2011/0130823 A1 | 6/2011 | Gerold et al. | |
| 2011/0137395 A1 | 6/2011 | Fargahi | |

FOREIGN PATENT DOCUMENTS

| | | |
|---|---|---|
| CN | 101385875 A | 3/2009 |
| CN | 101632842 A | 1/2010 |
| CN | 101721266 A | 6/2010 |
| DE | 102007030438 A1 | 1/2009 |
| EP | 1 270 023 A2 | 1/2003 |
| EP | 1795215 A2 | 6/2007 |
| EP | 1835043 A1 | 9/2007 |
| EP | 1959025 A1 | 8/2008 |
| EP | 2169090 A1 | 3/2010 |
| EP | 2189169 A1 | 5/2010 |
| JP | 2005253959 A | 9/2005 |
| WO | WO-2005102222 A2 | 11/2005 |
| WO | WO-2007136969 A2 | 11/2007 |
| WO | WO-2008106271 A2 | 9/2008 |

(56) References Cited

FOREIGN PATENT DOCUMENTS

| WO | WO-2008118606 A2 | 10/2008 |
|----|------------------|---------|
| WO | WO-2010017959 A2 | 2/2010  |
| WO | WO-2010132910 A1 | 11/2010 |

OTHER PUBLICATIONS

International Search Report and Written Opinion, Application No. PCT/US2011/062922, dated Oct. 26, 2012, 18 pages.

Partial International Search Report and Invitation to Pay Additional Fees, Application No. PCT/US2011/062922, dated Jul. 2, 2012, 9 pages.

Invitation to Pay Additional Fees with Partial International Search for International Application No. PCT/US2011/041258, mailed on Oct. 10, 2011, 5 pages.

Ohno, A. "Magnesium Ingot by Ohno Continuous Casting Process," Light Metal Age, Fellom, San Francisco, CA, US, vol. 46, No. 5/06, Jun. 1, 1988, p. 6/07.

M.H. Kim, H.H. Jo and H.Y. Cho, Operating parameters for the continuous unidirectional solidification of the Al-1 wt.% Si Alloy drawn to fine wire, Metals and Materials, vol. 6, No. 6 (2000), pp. 491-495.

X. Fan, Y. Cai Y, P. Wei, J. Li and H. Fu , Continuous casting technology of single crystal metals, Chinese Journal of Materials Research, Jun. 1996, vol. No. 3.

Y.J. Kim and S. Kou, An Experimental Study on Process Variables in Crystal Growth by Ohno Continuous Casting, Metallurgical Transactions A, vol. 19A, Jul. 1988—pp. 1849.

Z.M. Zhang, T.Lu, C.j. Xu and X.F. Guo, Microstructure of binary Mg—Al eutectic alloy wires produced by the Ohno continuous casting process, ACTA Metaql vol. 21, No. 4 pp. 275-281 Aug. 2008.

Japanese Patent Office—English translated office action for Japanese Application No. 2013-516690, May 28, 2014.

Motoyasu, Genjiro, "Development of Bioabsorbable Pure Magnesium Stent Material," Sci. Res. Fund-Sub. Proj. Database, Res. Per. Report of 2006, Res. Proj. No. 18650134 (2007).

Tajima, et al., "Tensile deformation of single crystal pure magnesium rods produced by the OCC process," 112th Spring Conf. of Japan Inst. of Light Metals, 357-358 (2007).

\* cited by examiner

BIOABSORBABLE IMPLANTS

RELATED APPLICATIONS

This application claims priority to, and the benefit of, U.S. Provisional Patent Application Ser. No. 61/398,030 filed Jun. 21, 2010, U.S. Provisional Patent Application Ser. No. 61/399,340 filed Jul. 12, 2010, and U.S. Provisional Patent Application Ser. No. 61/458,705, filed Dec. 1, 2010. The disclosures of all three of these provisional applications are incorporated by reference herein in their entireties.

FIELD OF THE INVENTION

This application relates generally to implants, and more specifically to bioabsorbable intraluminal implants.

BACKGROUND OF INVENTION

The field of coronary angioplasty and stenting has made dramatic progress in treatment of coronary heart disease through at least three generations of product technology. However, each generational advancement has been accompanied by a new challenge or failure mode of the therapy. Balloon angioplasty therapy improved acute luminal flow, but vessel recoil and remodeling resulted in high restenosis rates. Bare metal stenting lowered restenosis rates and minimized abrupt closure events, but restenosis rates were still high due to stent mechanical injury and resulting smooth muscle cell (SMC) migration and proliferation into the lumen. Drug eluting stents cut the retreatment rate again significantly by addressing the SMC proliferation with a pharmaceutical agent, but again was accompanied by a "new" complication, late stent thrombosis (LST) and the accompanying extended use of anti-coagulants. LST is associated with high mortality rates, although the frequency of the events is relatively low. The apparent factors driving this serious complication appear to be the loss of vaso-motion and delayed healing of a functional endothelium.

Attempts to use magnesium and its alloys as a temporary implant biomaterial, including in cardiovascular stents, have been hindered by poor control over the rate and uniformity of the metal's degradation (metallic corrosion rate), fragmentation and absorption processes in local tissue. Previous attempts to control degradation or corrosion rates have focused on alloying with rare earth and other heavy metal elements of unknown biocompatibility, yielding slower metallic corrosion rates but unproven benefits in clinical performance. Although these approaches have merit for non-medical applications such as commercial or aerospace castings, they are sub-optimal for an absorbable implant grade material that will eventually be fully metabolized by the host tissue, releasing alloying elements of unknown biocompatibility. Furthermore, conventional approaches to corrosion control of magnesium alloys have focused solely on preventing the initial mechanical failure of the given article by retarding the degradation process either by a surface passivation layer, or changing the local corrosion potential of the alloy. No consideration has been given to controlling the process of fragmentation, disintegration and absorption following the initial mechanical failure. For many implant applications, the timing and nature of the full degradation process, starting with the as-implanted metal article to the final clearance of the alloy mass and its degradants from the anatomical site, is critical regarding the performance of the medical device.

For absorbable metal implants, the corrosion process and ultimate mechanical properties are strongly dominated by the polycrystalline grain structure of the metal. Corrosion can proceed along grain boundaries due to localized galvanic reactions between Mg and more noble metals that are excluded from the crystal lattice during solidification from the melt. Cavitation and cracking can start at the grain boundaries due to the cyclic fatigue from pulsatile loading in the artery, resulting in gross mechanical failure of the implant long before a significant volume fraction of Mg has experienced corrosion. This can significantly shorten the implant's functional life, i.e., the period of time where the implant is mechanically intact and load bearing, and extend the time when large metallic fragments can cause injury and inflammation at the implant site.

One such implant application is absorbable metal stents for vascular or luminal scaffolding, such as stents for treatment of coronary artery disease. In this application, the stents provide a temporary scaffolding through the healing process related to the local injury caused by the high pressure angioplasty balloon used to open the stenosed or partially blocked artery. The metal scaffold is typically required only for a period of days to weeks to prevent abrupt closure of the vessel from spasm, minimize elastic recoil, and as a substrate to deliver a controlled release drug-polymer formulation to the site of injury. After this period, any remnant of the alloy or its degradants may be a liability, since it can act as a foreign body prolonging an inflammatory response and delaying healing. Furthermore, if the stent remnants remain present in the lumen in solid form through the period of extracellular matrix deposition and scar formation, then the stent remnants themselves become a source of lumen obstruction and participate in a new form of restenosis unknown to conventional permanent stents.

An alternative design approach towards absorbable stents utilizes highly crystalline absorbable polymers such as PLLA for the structural elements of the stent scaffold. This approach has a more controlled degradation process, but suffers from low radial stiffness that is needed to open the artery, i.e., so called acute gain, and limited ductility making stent-artery sizing problematic.

The current standard of care for treating most de novo coronary lesions is the implantation of a permanent implant known as a drug eluting stent or DES. The DES is a third generation angioplasty device for treating coronary stenosis, with significantly lower re-intervention rates than either bare metal stents or balloon angioplasty. This generation technology is a permanent implant, typically comprising a high strength and high radiopacity metal such as cobalt chrome or platinum enriched stainless steel, coated with a formulation of an anti-proliferative drug in a controlled release polymer.

The next generation of technology is a fully absorbable DES, i.e. the entire mechanical scaffolding (stent) and the drug formulation is broken down in the body and absorbed. The working hypothesis is that any permanent foreign body at the site can prolong inflammation and delay healing and restoration to its native state. The major complication associated with drug eluting stents is late stent thrombosis, which is believed to result from this delayed healing.

The primary focus of fully absorbable stents has been on achieving the necessary hoop strength and stiffness to bear the high mechanical stresses in the coronary arteries, but a second key characteristic that is required is radio-opacity to enable the physician to visualize the stent after implantation. Since the two primary materials used in experimental absorbable stents, L-poly lactic acid (pLLA) and magnesium alloys, are both essentially radio-transparent, small disc-shaped radio-markers comprised of platinum, platinum-iridium, or tantalum are typically integrated into the end of the laser cut stent body. If there are 2 or 3 radio-markers on each end of the stent, then the location and level of deployment can be visualized by angiography during a procedure, even if the bulk of the stent is not radio-opaque. This is a well established approach for nickel-titanium permanent stents which possessed low intrinsic radio-opacity.

The problems with this conventional approach for metallic absorbable stents, such as magnesium-based alloys, are that fragmentation occurs within weeks, and the relatively large radio-markers (approximately 1.0 mm diameter by 125 micron thick) may migrate from the implantation site and become emboli, potentially resulting in a serious infarction of distal coronary vessels. Ideally, the radio-marker for an absorbable magnesium stent would be self-sufficient regarding prevention of migration, and its safety not be compromised through magnesium fragmentation process.

SUMMARY OF INVENTION

The use of magnesium and its alloys, as well as alloys of iron, zinc, calcium, and manganese, as an absorbable biomaterial for temporary implants has been hindered by poor control over the rate and uniformity of the metals strength and mass loss. A novel approach described herein improves these properties through processing by directional solidification and the formation of single crystal or poly-columnar crystal micro-structures. The resulting structure degrades primarily by surface erosion, whereas conventional polycrystalline metal breaks rapidly along grain boundaries resulting in early mechanical failure, followed by slow full absorption.

In particular, embodiments of the invention address the deficiencies of conventional polycrystalline metal-based alloys of magnesium, iron, zinc, calcium, and manganese for elongated implants through control of the microstructure to yield either single crystal or columnar crystal structures that extend continuously for the length of the implant or implant sub-component. This structure yields a more controlled and uniform strength retention and degradation profile than conventional polycrystalline structures, which rapidly lose strength due to corrosion along grain boundaries but then have long absorption times due to the slow corrosion rate of the bulk of the alloy within the individual grains. In some embodiments, the implants of this invention lose strength and mass in parallel as the cross-sectional area is reduced through surface erosion.

Moreover, a fourth generation of cardiovascular implants are described; these implants are based on bioabsorbable stent scaffolds that may resolve both the vaso-motion and foreign body issues, by fully absorbing in a period of 3-24 months post-implantation.

Embodiments of the invention address the deficiencies of previous absorbable intra-luminal implants for local drug delivery by a composite design that utilizes absorbable metal and absorbable polymer technologies. The design includes a plurality of discrete rings or a continuous helix of ring-like structures formed of an absorbable metal, such as magnesium, zinc, or iron and their respective alloys, to achieve high radial force and stiffness necessary to prevent vessel recoil. Unlike current metal stents, the structural rings are not interconnected by metal elements, but instead by flexible absorbable polymer connectors with a different absorption time than the metal ring elements. Finally, the device serves as a drug delivery substrate by inclusion of an active pharmaceutical, preferably an anti-proliferative agent to smooth muscle cells that is eluted at a controlled rate over a period of weeks to months.

Embodiments of the invention include a hybrid intraluminal implant that consists of a plurality of cylindrical or "ring" segments, with alternating segments of bioabsorbable and biostable (permanent, nondegrading) materials. The "end" segments (proximal and distal) include a biostable and radio-opaque material such as a cobalt chrome alloy or stainless steel, and at least one inner ring segment comprising or consisting essentially of bioabsorbable material such as magnesium or its alloys. The ring segments are connected by polymeric connectors to avoid uncontrolled galvanic reactions between the permanent and absorbable metals in the presence of physiological fluid containing chlorides (saline). The implant's utility is enhanced by incorporation of an anti-proliferative drug with sustained release.

The acute performance of the hybrid stent is similar to conventional DES implants regarding acute luminal gain. The bioiabsorbable segments are fully absorbed in 6 months allowing endothelial healing and return of vaso-motion. The biostable ring segments are permanent radiomarkers that are self-sufficient for preventing migration and embolization. The biostable segments also provide load sharing to the adjacent absorbable metal segments through the polymer connectors, reducing lumen loss during the absorbable segment fragmentation period.

In an aspect, embodiments of the invention include a bioabsorbable implant including an elongated metallic element having more than about 50% by weight the metal magnesium, iron, zinc, calcium, or manganese, and/or combinations or alloys thereof and being substantially free of rare earth metals, namely the 15 lanthanoid elements, i.e., the elements having a proton number of 57-71, scandium, and yttrium. The elongated metallic element may define at least a portion of the bioabsorbable implant.

One or more of the following features may be included. The metal may define a continuous single grain and/or a columnar microstructure. The metal may define a columnar microstructure including grains having an average grain length of at least about 1 mm, and an average grain diameter of less than about 0.2 mm. The average grain length may be at least about 10 mm and/or the average grain diameter may be less than about 3 mm. The continuous single grain may have an aspect ratio of grain length to grain diameter of at least 10:1. The columnar microstructure may include grains having an aspect ratio of grain length to grain diameter of at least 10:1.

The elongated metallic element may a wire, rod, and/or a hollow tube. The wire may have a diameter of less than about 0.2 mm.

The bioabsorbable implant may be an intraluminal device, a ligating clip, a ligating clip component, a bone fixation device (e.g., a plate, a pin, or a screw), or a bone-to-soft-tissue fixation device (e.g., a suture anchor, an interference screw, and a cross pin).

The description of elements of the embodiments of other aspects of the invention may be applied to this aspect of the invention as well.

In another aspect, embodiments of the invention include a bioabsorbable implant including an elongated metallic element having more than about 50% by weight a metal and being substantially free of rare earth elements, the elongated metallic element defining at least a portion of the bioabsorbable implant and including a wire formed into a bioabsorbable continuous helical sinusoid.

One or more of the following features may be included. The metal may be magnesium, iron, zinc, calcium, or manganese and/or combinations or alloys thereof. The wire may define at least one of a continuous single grain and a columnar microstructure.

The description of elements of the embodiments of other aspects of the invention may be applied to this aspect of the invention as well.

In yet another aspect, embodiments of the invention include a bioabsorbable implant including an elongated metallic element having more than about 50% by weight a metal and being substantially free of rare earth elements. The elongated metallic element may define at least a portion of the bioabsorbable implant and may include a wire formed into a first bioabsorbable expandable metal ring and a second bioabsorbable expandable metal ring. The bioabsorbable implant may also include at least one flexible longitudinal connecter including an absorbable polymer and connecting the first and second expandable metal rings. A coating including a pharmaceutically active agent may be disposed over at least a portion of at least one of the first and second metal rings and the longitudinal connector.

One or more of the following features may be included. The metal may be magnesium, iron, zinc, calcium, or manganese, and/or combinations or alloys thereof. At least one of the expandable metal rings comprises a wire and may define a single grain and/or a columnar microstructure. At least one of the expandable metal rings may include a stud configured for coupling with an adjacent feature.

The at least one flexible longitudinal connector may include a biodegradable homopolymer and/or a aliphatic polyester such as lactic acid, lactide, glycolic acid, glycolide, caprolactone, dioxanone, trimethylcarbonate, and co-polymers and blends thereof.

The at least one flexible longitudinal connector may include directionally oriented absorbable filaments extending along a length of the bioabsorbable implant and/or extruded tubes of absorbable polymer. At least one of the expandable rings may form an aperture adapted for coupling with the at least one flexible longitudinal connector.

The pharmaceutically active agent may include or consist essentially of, e.g., a potent anti-proliferative to human smooth muscle cells, taxane, an mTOR agent, and/or a chemoactive agent suitable for cancer treatment.

The description of elements of the embodiments of other aspects of the invention may be applied to this aspect of the invention as well.

In another aspect, embodiments of the invention may include a bioabsorbable implant including an elongated metallic element having more than about 50% by weight a metal and being substantially free of rare earth elements. The elongated metallic element may define at least a portion of the bioabsorbable implant, and may include a wire formed into a discrete bioabsorbable expandable metal ring. The bioabsorbable implant may also include at least two biostable ring elements, each biostable ring including a biostable and radio-opaque metallic alloy, with the bioabsorbable expandable metal ring being disposed adjacent at least one of the biostable rings. At least one flexible longitudinal connecter including a bioabsorbable polymer may be disposed between at least two adjacent rings. A coating including at least one pharmaceutically active agent may be disposed over at least a portion of one ring.

One or more of the following features may be included. The metal may be magnesium, iron, zinc, calcium, or manganese, and/or combinations or alloys thereof. At least two of the biostable rings may include a laser-machined hypo-tube made of, e.g., cobalt, chrome, stainless steel, titanium, or iron and/or alloys thereof.

At least one of the discrete biostable rings may define an aperture and/or a stud configured to couple with the at least one flexible longitudinal connector.

The at least one flexible longitudinal connector may include a biodegradable homopolymer and/or an aliphatic polyester, e.g., lactic acid, lactide, glycolic acid, glycolide, caprolactone, dioxanone, trimethylcarbonate, and co-polymers and blends thereof. The at least one flexible longitudinal connector may include directionally oriented absorbable filaments extending along a length of the bioabsorbable implant and/or extruded tubes of absorbable polymer.

The pharmaceutically active agent may include or consist essentially of a potent anti-proliferative to human smooth muscle cells, taxane, an mTOR agent, and/or a chemoactive agent suitable for cancer treatment.

The description of elements of the embodiments of other aspects of the invention may be applied to this aspect of the invention as well.

BRIEF DESCRIPTION OF DRAWINGS

The following drawings are not necessarily to scale, emphasis instead being placed generally upon illustrating the principles of the invention. The foregoing and other features and advantages of the present invention, as well as the invention itself, will be more fully understood from the following description of exemplary and preferred embodiments, when read together with the accompanying drawings, in which.

DETAILED DESCRIPTION

Figure 1:
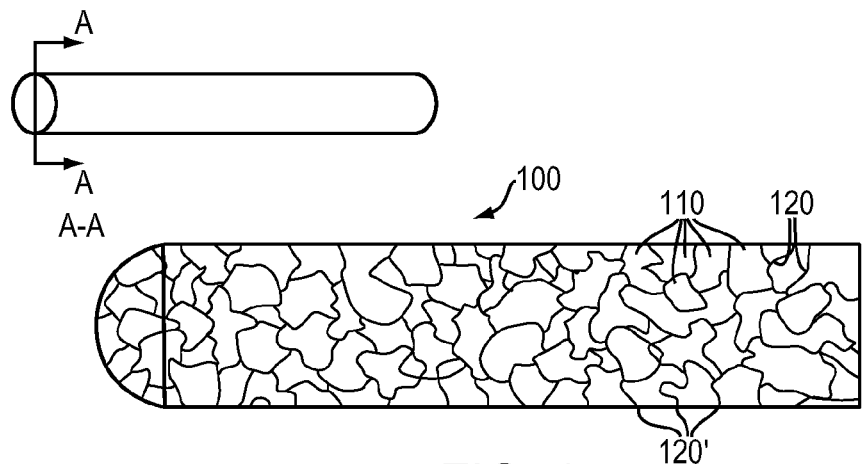
FIG. 1 is a schematic diagram of a segment of an elongated implant or sub-component such as a wire or pin with a conventional polycrystalline grain structure.

Referring to FIG. 1, a segment of an elongated implant 100 or sub-component such as a wire or pin with a conventional polycrystalline grain structure in cross-section A-A, has a plurality of grains 110 separated by grain boundaries 120. Grain boundaries 120' that are aligned perpendicularly to the primary loading axis may be initiation points for premature failure due to accelerated corrosion or crack formation from fatigue.

Figure 2:
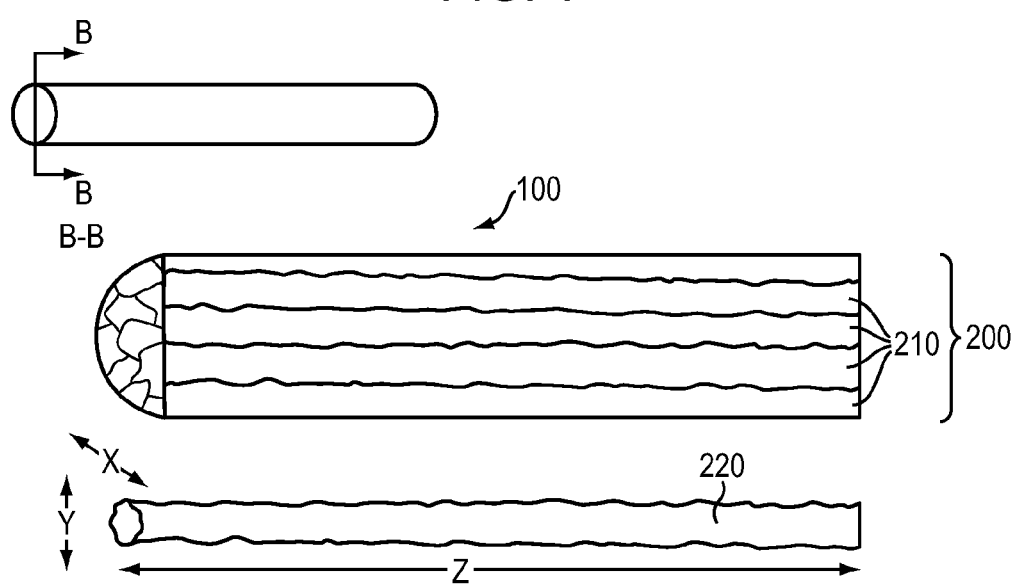
FIG. 2 is a schematic diagram of a segment of an elongated implant or sub-component processed by directional solidification that yields a plurality of columnar crystals in accordance with an embodiment of the invention.

In contrast, the crystal structure in accordance with embodiments of the invention may be either single crystal (i.e., a continuous single grain) or columnar crystal structures (i.e., a columnar microstructure) that extend continuously for the length of the implant or implant sub-component. Referring to FIG. 2, a bioabsorbable implant may include an elongated metallic element or sub-component that may be formed by directional solidification that yields a columnar microstructure 200 plurality of columnar crystals 210 that extend essentially the full functional length of the implant 100. A single crystal structure 220 that is essentially without grain boundaries is shown for clarity, with dimensions of z>>x, z>>y.

If the metal defines a columnar microstructure 200, the columnar microstructure may include grains having an average grain length of preferably at least about 1 mm, and an average grain diameter of preferably less than about 0.1 mm.

In some embodiments, the average grain length may be at least about 10 mm. The average grain diameter is at least about 5 mm. The metal may include one or more grains having an aspect ratio of grain length to diameter of at least 10:1, preferably 100:1 or more.

To achieve such a controlled microstructure, the implant or implant sub-component may processed from a melt by a process that controls the direction of solidification along its elongated axis. This may be achieved through controlled heat removal (under-cooling) at one end of the elongated structure so that crystal nucleation and propagation is driven down its length (z axis in FIG. 2), while crystal formation in the directions perpendicular to elongated axis are retarded by keeping those surfaces at an elevated temperature with insufficient under-cooling for nucleation. Additional mechanical forming processes can be practiced following directional solidification to achieve the final implant geometry, if the thermal treatments do not result in a re-crystallization that reverts the structure to polycrystalline.

A suitable process for forming at least a portion of an implant from a melt is the Ohno process. The Ohno process, typically used to form copper wires, is described in the literature. See, e.g.:

1. A. Ohno Casting of Near Net Shape Products, Edited by Y. Bahai, The Metallurgical Society (1988) 177;
2. X. Fan, Y. Cai Y, P. Wei, J. Li and H. Fu, Continuous casting technology of single crystal metals, Chinese Journal of Materials Research (June 1996) Vol. 10, No. 3, pp. 264-266;
3. Z. M. Zhang, T. Lu, C. J. Xu and X. F. Guo, Microstructure of binary Mg—Al eutectic alloy wires produced by the Ohno continuous casting process, ACTA Metall. Sin. (Engl. Lett.) Vol. 21, No. 4 (August 2008) pp. 275-281;
4. M. H. Kim, H. H. Jo and H. Y. Cho, Operating parameters for the continuous unidirectional solidification of the Al-1 wt. % Si Alloy drawn to fine wire, Metals and Materials, Vol. 6, No. 6 (2000) pp. 491-495; and
5. Y. J. Kim and S. Kou, An Experimental Study on Process Variables in Crystal Growth by Ohno Continuous Casting, Metallurgical Transactions A, Volume 19A (July 1988) pp. 1849. Each of these references is incorporated by reference herein in its entirety.

In particular, the Ohno process is a continuous casting process that uses a heated mold, rather than a cooled mold. The mold is heated slightly above the melting point of the metal to be solidified. This has the result that no new grains can nucleate at the mold wall. Solidification is restricted to the contact area between the melt and the dummy rod or single crystal seed, which is withdrawn from the melt. The mold can be positioned either vertically upward, vertically downward, or horizontal. The melt stays in the mold even when the mold is not positioned vertically upward, as the die diameter is small, and grips or pinch rollers are needed to pull the wire out of the mold.

An advantage of the Ohno process is that it can be used for directional solidification or crystal growth, and ingots or crystals of unlimited length may be produced. The resulting material has a smooth surface and inner quality due to the fact that impurities are moved to the boundaries, resulting in a pure crystal. In addition superior mechanical properties are achieved due to the resulting directionally solidified microstructure.

One way to create a wire using the Ohno process is to utilize a crucible furnace with a melt level control, a heated mold with a small diameter channel, a cooling device to cool the wire after it exits the mold, and pinch rolls to pull the wire away from the mold.

Wire/bar drawing, a metalworking process known to those of skill in the art, allows for successive reductions in diameter of the bar/wire by pulling the wire/bar through successively smaller diameter dies. The successive reductions in diameter result in expansion of the length of the wire. The die is typically mounted on a draw bench and the end of the wire is placed in grips so that the rest of the wire may be pulled through the die. The process of drawing improves the mechanical properties of the wire due to work hardening.

In an exemplary process, eutectic Mg—Al wires of 5 mm in diameter with mirror-smooth surface may be continuously solidified with a casting speed 10 mm/min, a mold exit temperature of 450° C., a static pressure head of the melt of 5 mm, a flow rate of cooling water 30 L/h, and a mold-cooling water distance 20 mm. Under these casting conditions, the wires solidify just outside of the mold exit.

Various metals may be suitable for embodiments of the invention, including metallic alloys of magnesium, iron, zinc, calcium, manganese and/or combinations thereof. In particular, an elongated metallic element may include more than about 50% by weight a metal, such as magnesium, iron, zinc, calcium, and/or manganese metals and/or combinations or alloys thereof, and is preferably substantially free of rare earth metals. Substantially free of rare earth metals, as used herein, means that less than 0.1% (by weight) of the metallic alloys includes rare earth metals. Anything less than 0.1% is in the hundreds parts per million range, which is below the FDA threshold in safety profiles of individual impurities in drugs. At that level, rare earth metals also do not have a significant effect on corrosion properties. Rare earth and other high atomic number metals and their compounds are undesirable in implants because they are largely insoluble in physiologic fluids, which significantly delays absorption by local tissue.

In some embodiments, the metallic alloy may be at least 80% Mg, with the balance including one or more of the elements Ca, Mn, Zn, Fe, plus trace elements. It may be preferable to use pure Mg as a basis for the alloy, with no inclusion of rare earth metals.

Figure 3:
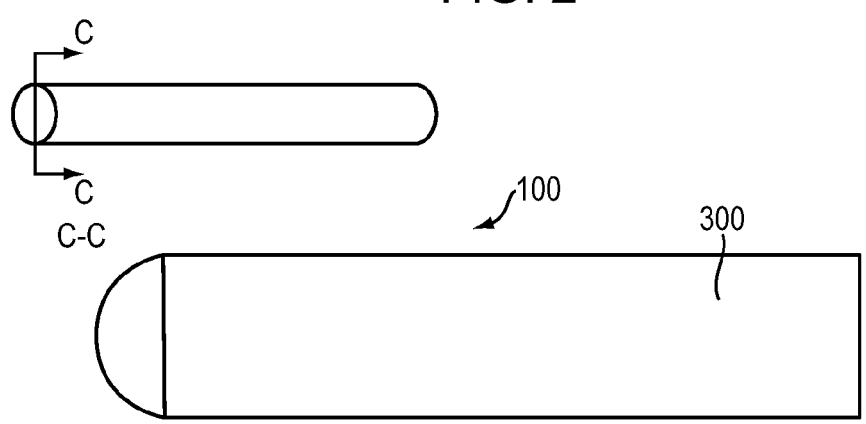
FIG. 3 is a schematic diagram of an elongated implant or sub-component formed of a single crystal that is essentially without grain boundaries in accordance with an embodiment of the invention.

Referring to FIG. 3, in some embodiments, a segment of an elongated implant or sub-component processed by directional solidification yields a single columnar crystal 300 that extends essentially the full functional length of the implant.

The elongated metallic element may define at least a portion of the bioabsorbable implant. The elongated metallic element may include a wire. The wire may have a diameter of less than about 0.2 mm. For intraluminal devices like stents, diameters above about 0.2 mm may create too much trauma to the vessel wall. On the other hand, in some embodiments such as ligating clips or suture anchors, diameters up to several mm may be preferred.

As discussed below, the elongated metallic element may include a wire formed into at least one discrete bioabsorbable expandable metal ring, or a wire formed into a bioabsorbable continuous helical sinusoid. The metal ring may be formed from welded wire forms or by laser micro-machining of metal tubing.

Figure 4:
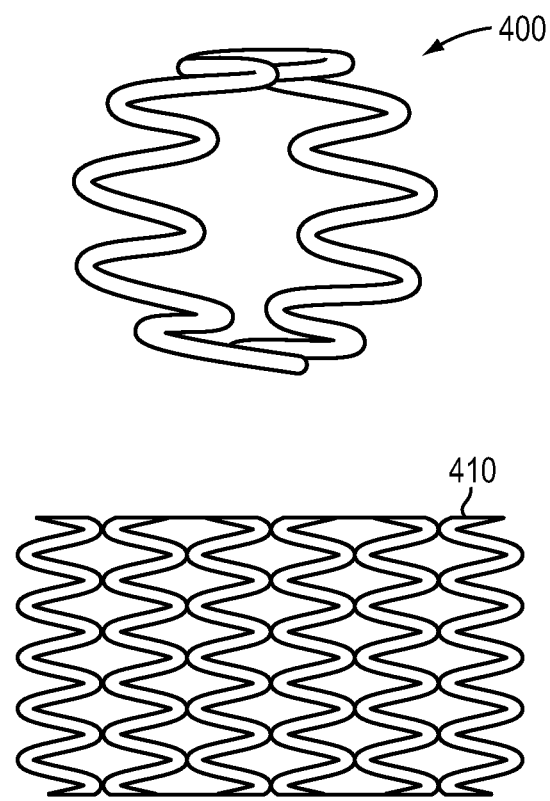
FIG. 4 is a schematic diagram of a segment of directionally solidified alloy formed into a sub-component of an implant, in accordance with an embodiment of the invention.

The bioabsorbable implant may be any one of various devices, such as an intraluminal device. Referring to FIG. 4, a segment of directionally solidified alloy may be formed into a sub-component of an implant, i.e., a ring element 400 of a balloon expandable coronary stent 410.

Figure 5:
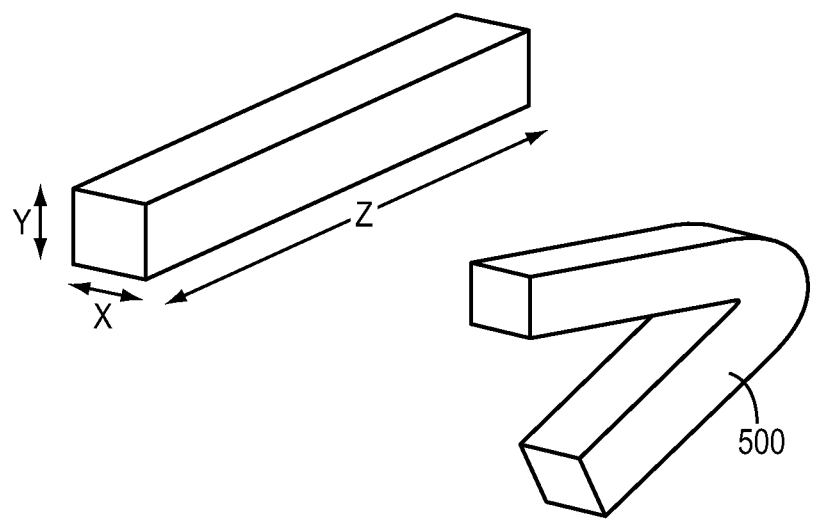
FIG. 5 is a schematic diagram of a segment of directionally solidified alloy formed into a ligating clip, in accordance with an embodiment of the invention.
Figure 5:
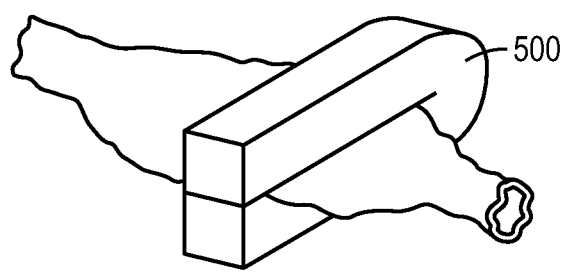

The bioabsorbable implant may also be a ligating clip or a ligating clip component. In particular, referring to FIG. 5, a segment of directionally solidified alloy may be formed into a ligating clip 500 for tubular anatomical structures.

Figure 6:
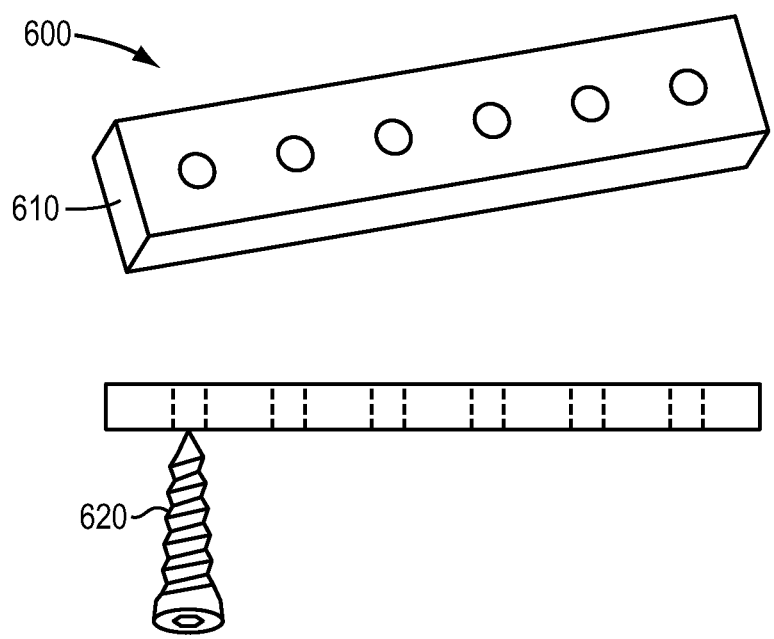
FIG. 6 is a schematic diagram of directionally solidified alloy formed into a bone fixation device, in accordance with an embodiment of the invention.

Referring to FIG. 6, in some embodiments, the bioabsorbable implant is a bone fixation device 600 for fracture fixation, e.g., a plate 610, a pin, or a screw 620.

Figure 7:
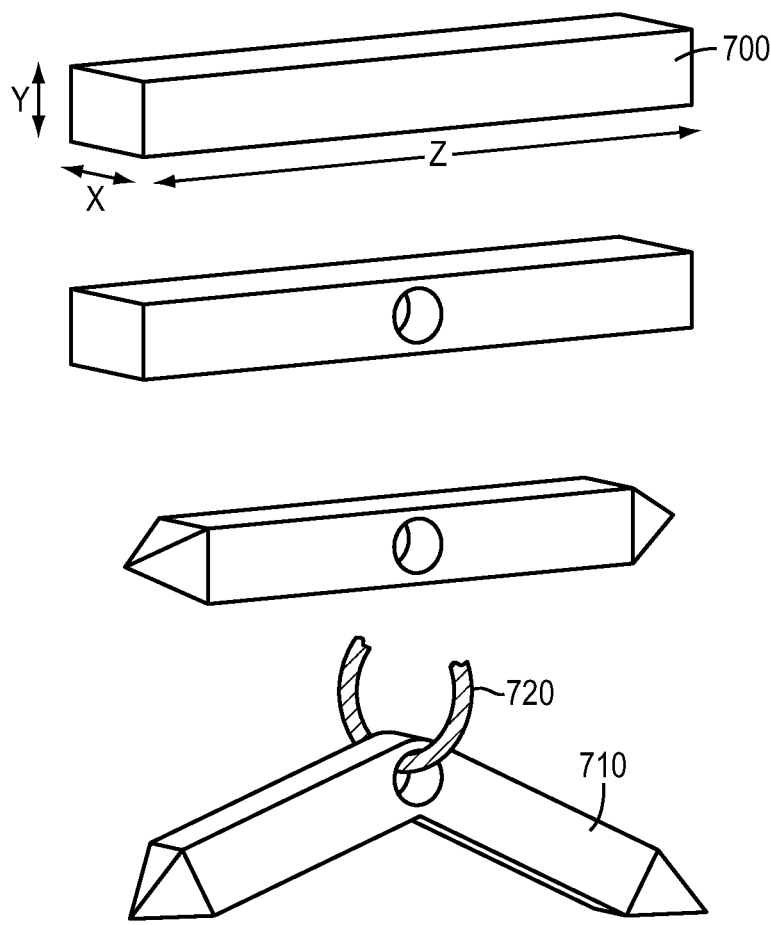
FIG. 7 is a schematic diagram of a segment of directionally solidified alloy blank formed into a bone anchor, in accordance with an embodiment of the invention.

In other embodiments, the bioabsorbable implant is a bone-to-soft-tissue fixation device, e.g., a suture anchor, an interference screw, or a cross pin. For example, referring to FIG. 7, a segment of directionally solidified formed alloy, produced as discussed above, in the form of a blank 700 may be formed into a bone anchor 710 (also referred to as a suture anchor) for soft tissue reattachment by means of a suture 720.

Several key features of the directionally solidified structures differentiate their performance from polycrystalline alloys of the same alloy composition and geometry (cross-sectional area). First, they retain strength and physical integrity longer under corrosion conditions (in vivo) due to the elimination of vulnerable grain boundaries that contain Fe and other impurities that result in mini-galvanic cells with the Mg. For many implant applications, maintaining strength and integrity through the early healing periods is critical for both soft and hard tissue applications.

Secondly, they inherently possess better ductility and fatigue resistance, since mechanical failure (in the absence of corrosion) is most often initiated at a micro-crack that forms at the interface of two grains under tensile or compressive load. This feature of directionally solidified alloys is currently utilized for critical load bearing non-implant applications such as turbine rotors.

Thirdly, because the loss of strength and mass is through surface corrosion and erosion, they degrade more "gracefully" in vivo, i.e. fragmentation starts later and with smaller and less injurious intermediate fragments.

Figure 8A:
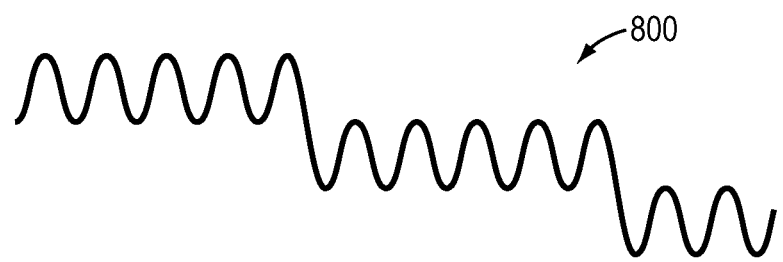
FIG. 8a is a schematic diagram of a wire formed into a continuous sinusoidal-like wave form in accordance with an embodiment of the invention.
Figure 8B:
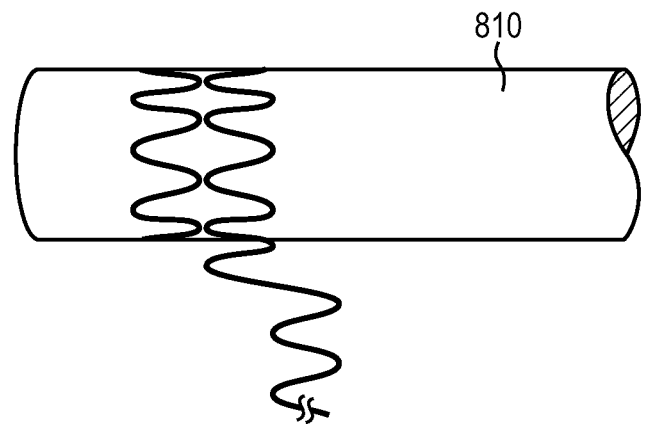
FIG. 8b is a schematic diagram illustrating the continuous sinusoidal-like wave form of FIG. 8a being wrapped around a mandrel, in accordance with an embodiment of the invention.
Figure 8C:
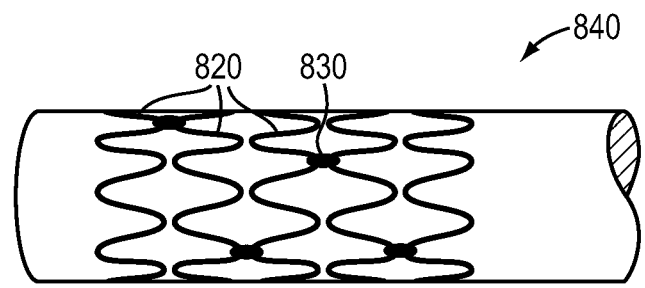
FIG. 8c is a schematic diagram of a bioabsorbable continuous helical sinusoid, in accordance with an embodiment of the invention.

A preferred embodiment of a bioabsorbable implant is a bioabsorbable helical continuous sinusoid. This structure may include a wire formed into the sinusoid; the wire may define either a continuous single grain or a columnar microstructure. Referring to FIGS. 8*a* and 8*b*, a helical continuous sinusoid may be defined as a wire-form tubular structure made from a wire that is first formed into a continuous sinusoidal-like wave form 800, and that is secondly wrapped in a helical configuration around a cylindrical mandrel 810 to form a tubular but mechanically unstable structure. Referring to FIG. 8*c*, thirdly, the adjacent rows of ring-like structures 820 of the wire wave form 800 are connected at discrete contact points 830 to provide mechanical integrity, either by longitudinal absorbable polymer connectors, or by known metal welding techniques to define a helical continuous sinusoid 840.

A pharmaceutically active agent may be disposed over at least a portion of the helical continuous sinusoid 840. The pharmaceutically active agent may be one of many suitable materials. For example, it may be a potent anti-proliferative to human smooth muscle cells, and a chemoactive agent suitable for cancer treatment. The agent may be a taxane, such as Paclitaxel, its derivatives and prodrugs thereof. In some embodiments, the agent may be a known mTOR agent such as sirolimus or everolimus, their derivatives and prodrugs thereof. The implant may locally deliver both a taxane and a mTOR agent. The active agent may be eluted at a controlled rate through formulation with a biodegradable polymer.

One key aspect of one design in accordance with an embodiment of the invention is a more controlled, graceful degradation process than that of existing fully absorbable metal stent designs. In previous attempts to form absorbable metal stents, the integral metal longitudinal connecting elements degraded at a similar rate to the structural ring elements. At intermediate fragmentation stages, long and wide stent fragments may be formed consisting of multiple ring fragments and intact metal connectors. The shape and size of these fragments make them problematic relative to obstructing the vessel lumen. In one embodiment, the fragment size is reduced by using longitudinal connectors comprised of an absorbable polymer with significantly faster degradation kinetics than the metal rings. In another embodiment, the high surface area and favorable surface chemistry of the polymeric longitudinal connectors contribute to rapid tissue coverage and integration of the implant into the vessel wall.

Figure 9:
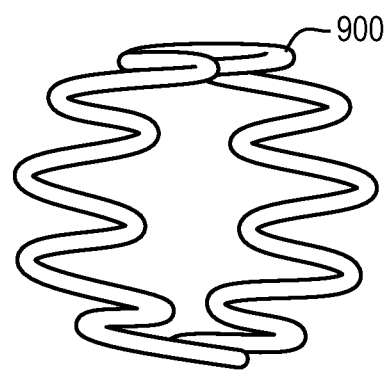
FIG. 9 is a schematic diagram of a single expandable ring made of an absorbable magnesium alloy wire that has been mechanically formed and welded in accordance with an embodiment of the invention.

Referring to FIG. 9, a single discrete bioabsorbable expandable metal ring 900 may be made from a wire of an absorbable magnesium alloy wire that has been mechanically formed and welded. The ring 900 may also be formed from any of the other alloys discussed above, including iron, zinc, calcium, and/or manganese metals or alloys, or any other material suitable for forming a bioabsorbable implant.

Figure 10:
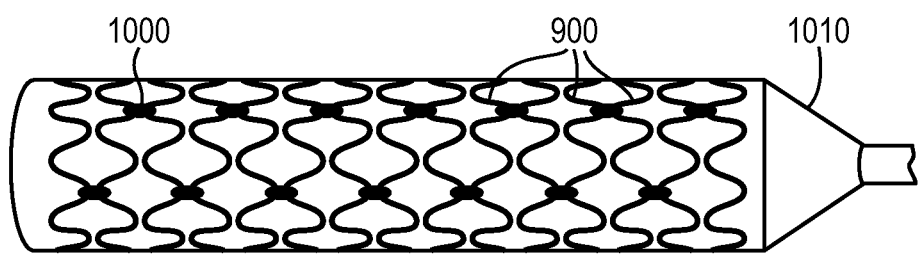
FIG. 10 is a schematic diagram of a plurality of expandable metal rings connected by discrete loops of absorbable polymer in accordance with an embodiment of the invention.

Referring to FIG. 10, a plurality of expandable metal rings 900 formed from wire may be connected by discrete loops of absorbable polymer, i.e., flexible longitudinal connector 1000, and mounted on a balloon catheter 1010. The plurality of rings may include a first discrete bioabsorbable expandable metal ring and a second discrete bioabsorbable expandable metal ring, with at least one flexible longitudinal connecter, including an absorbable polymer, connecting the first and second discrete expandable metal rings. A coating including a pharmaceutically active agent may be disposed over at least a portion of at least one of the first and second metal rings and the longitudinal connector. At least one of the expandable metal rings may include a wire defining a single grain or a columnar microstructure.

One or more of the flexible longitudinal connectors may include a biodegradable homopolymer of an aliphatic polyester, such as lactic acid, lactide, glycolic acid, glycolide, caprolactone, dioxanone, trimethylcarbonate, and co-polymers and blends thereof.

The pharmaceutically active agent may be one of many suitable materials. For example, it may be a potent anti-proliferative to human smooth muscle cells, and a chemoactive agent suitable for cancer treatment. The agent may be a taxane, such as Paclitaxel, its derivatives and prodrugs thereof. In some embodiments, the agent may be a known mTOR agent such as sirolimus or everolimus, their derivatives and prodrugs thereof. The implant may locally deliver both a taxane and a mTOR agent. The active agent may be eluted at a controlled rate through formulation with a biodegradable polymer.

Figure 11:
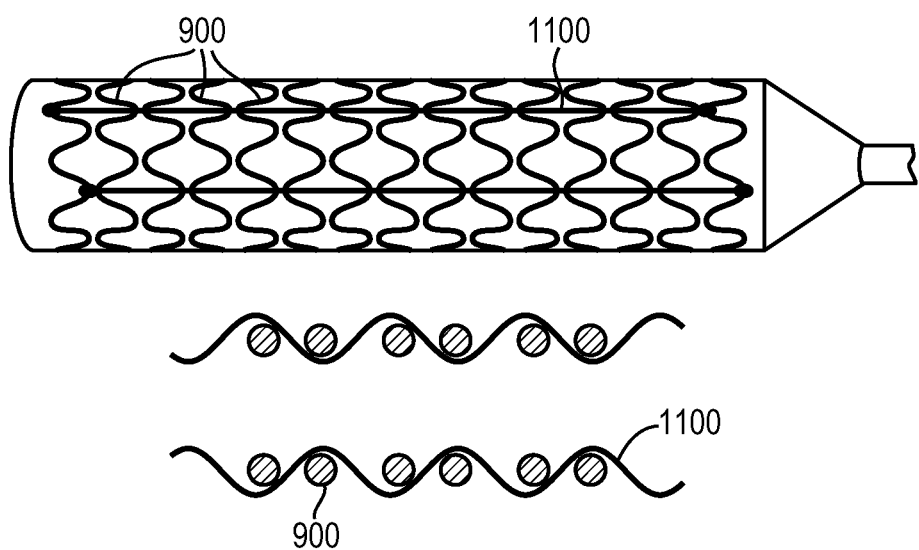
FIG. 11 is a schematic diagram of a plurality of expandable metal rings connected longitudinally by interwoven filaments made of absorbable polymer, with connectors extending continuously the full length of the implant in accordance with an embodiment of the invention.

Referring to FIG. 11, a plurality of expandable metal rings 900 or a helical continuous sinusoid may be connected longitudinally by interwoven filaments 1100 made of absorbable polymer. A longitudinal cross-sectional view shows the metallic rings 900 and interwoven filaments 1100. The helical continuous sinusoid 840 may also be similarly connected longitudinally by interwoven filaments 1100 (not shown).

At least one of the flexible longitudinal connectors may include directionally oriented absorbable filaments extending along a length of the bioabsorbable implant.

Figure 12A:
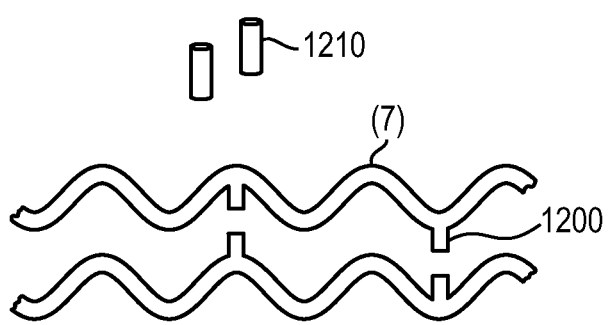
FIG. 12*a* is a schematic diagram of segments of expandable metal rings with stud features and a small diameter extruded tube of flexible absorbable polymer cut to length in accordance with an embodiment of the invention.
Figure 12B:
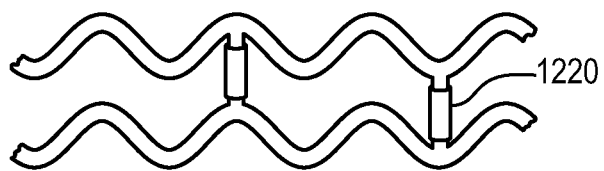
FIG. 12*b* is a schematic diagram of an assembled composite implant with the tube connecting the stud features on adjacent segments in accordance with an embodiment of the invention.

Referring to FIGS. 12a and 12b, at least one of the expandable metal rings 900 may define a stud feature 1200. The stud is configured to allow for mechanical connection of adjacent ring segments. A hollow, small diameter extruded tube of, e.g., flexible absorbable polymer of PLGA may be cut to length 1210 and interference fit over the opposing stud features 1200 to form a longitudinal connector 1220.

Figure 13:
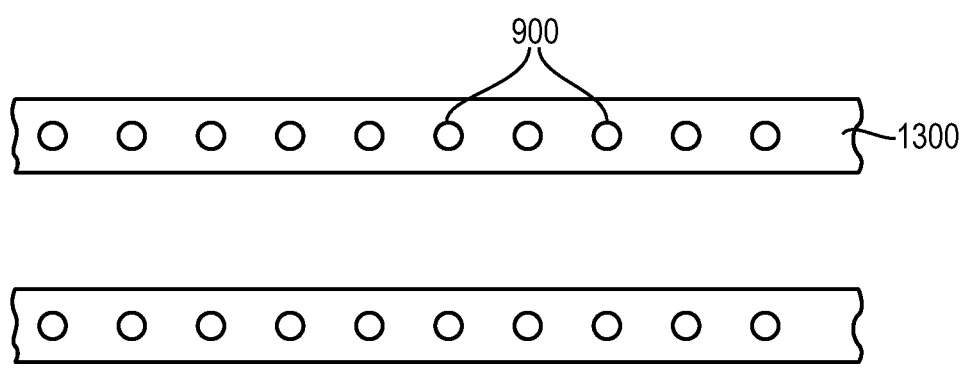
FIG. 13 is a longitudinal cross sectional view of a plurality of expandable metal rings connected by injection-molded longitudinal connectors of flexible absorbable polymer in accordance with an embodiment of the invention.

Referring to FIG. 13, a plurality of expandable metal rings 900 or a helical continuous sinusoid 840 may be connected by injection-molded longitudinal connectors 1300 of flexible absorbable polymer. Accordingly, in some embodiments, the flexible longitudinal connectors may include extruded tubes of absorbable polymer.

Figure 14:
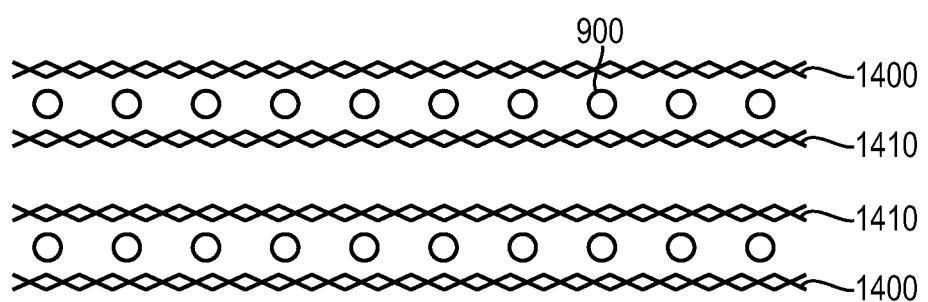
FIG. 14 is a longitudinal cross-sectional view of a 3-layer sandwich construction of braided absorbable polymer filaments on outer and inner layers, encapsulating a middle layer of expandable metal rings in accordance with an embodiment of the invention.

Referring to FIG. 14, a 3-layer sandwich construction may include braided absorbable polymer filaments on outer 1400 and inner layers 1410, encapsulating a middle layer of expandable metal rings 900.

In some embodiments, at least one of the expandable rings form an eyelet adapted for coupling with the at least one flexible longitudinal connector (see eyelet 5 in FIG. 14).

Figure 15:
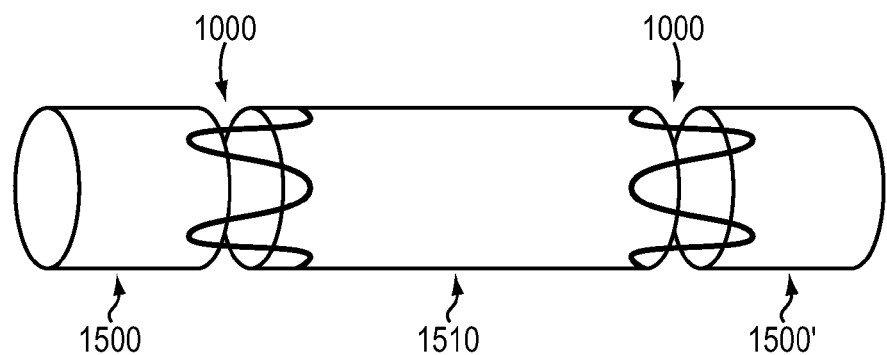
FIG. 15 is a schematic diagram of a hybrid stent including thin ring segments made from a biostable and radio-opaque material, a larger center ring segment made from an absorbable magnesium alloy, and filament connectors between segments made of absorbable polymer in accordance with an embodiment of the invention.

Referring to FIG. 15, a hybrid stent may include thin proximal and distal ring segments 1500, 1500' made from a biostable and radio-opaque material, a larger center ring segment 1510 including, e.g., a plurality of rings 900 made of a bioabsorbable magnesium alloy (or any or the other bioabsorbable alloys discussed herein) or a helical continuous sinusoid 840, and filament connectors, e.g., longitudinal connectors 1000 made of a bioabsorbable polymer such as PLGA. As seen in the figure, the bioabsorbable expandable metal ring 900 may be disposed adjacent at least one of the biostable rings 1500, 1500', and at least one flexible longitudinal connecter 1000 is disposed between at least two adjacent rings. A coating including at least one pharmaceutically active agent may be disposed over at least a portion of one ring.

At least one of the biostable rings may be a laser-machined hypo-tube including cobalt, chrome, stainless steel, titanium, and/or iron.

At least one of the flexible longitudinal connectors may include a biodegradable homopolymer and/or an aliphatic polyester such as lactic acid, lactide, glycolic acid, glycolide, caprolactone, dioxanone, trimethylcarbonate, and/or co-polymers and blends thereof.

At least one of the flexible longitudinal connectors may include directionally oriented absorbable filaments extending along a length of the bioabsorbable implant and/or extruded tubes of absorbable polymer such as PLGA.

As in other embodiments described herein, the pharmaceutically active agent may be one of many suitable materials. For example, it may be a potent anti-proliferative to human smooth muscle cells, and a chemoactive agent suitable for cancer treatment. The agent may be a taxane, such as Paclitaxel, its derivatives and prodrugs thereof. In some embodiments, the agent may be a known mTOR agent such as sirolimus or everolimus, their derivatives and prodrugs thereof. The implant may locally deliver both a taxane and a mTOR agent. The active agent may be eluted at a controlled rate through formulation with a biodegradable polymer.

Figure 16:
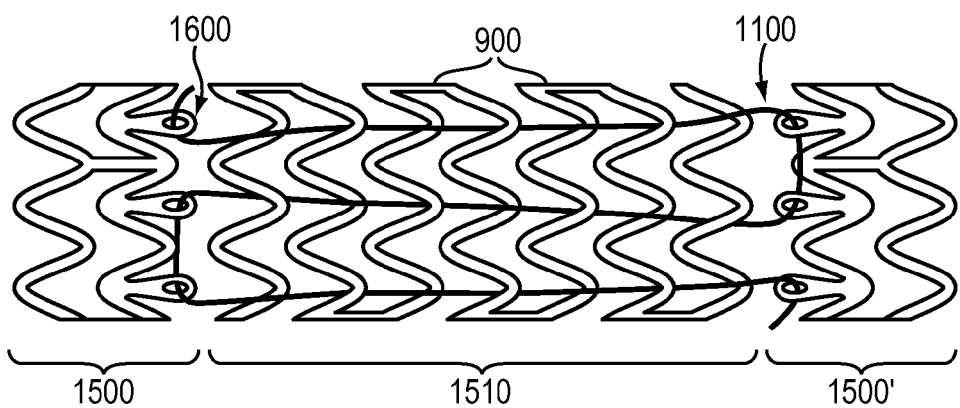
FIG. 16 is a schematic diagram of eyelet design features that facilitate the interlacing of ring segments by continuous filament connectors in accordance with an embodiment of the invention.

Referring to FIG. 16, at least one of the discrete biostable rings 1500, 1500' may define an eyelet 1600 and/or a stud configured to couple with at least one flexible longitudinal connector, e.g., interwoven filaments 1100. The eyelet design features 1600 facilitate the interlacing of the laser cut biostable proximal and distal ring segments 1500, 1500' by continuous filament connectors 1100 that transverse the center bioabsorbable segment 1510 including a plurality of bioabsorbable rings 900 or a helical continuous sinusoid 840.

Figure 17:
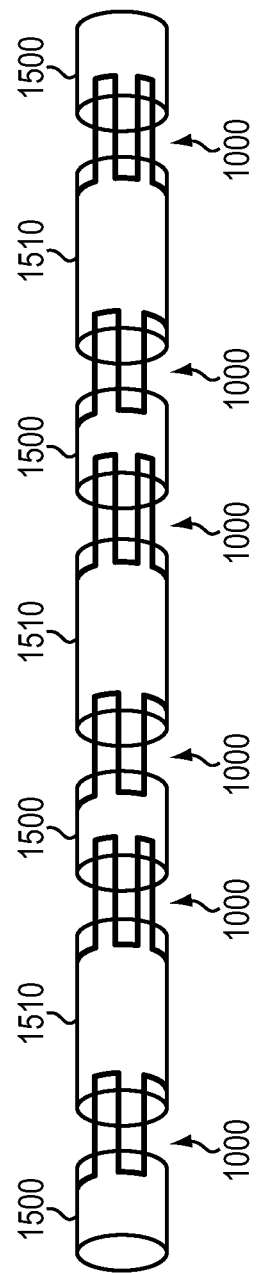
FIG. 17 is a schematic diagram of a hybrid stent with a plurality of alternating biostable and absorbable ring segments and absorbable polymer connectors in accordance with an embodiment of the invention.

Referring to FIG. 17, a hybrid stent may include a plurality of alternating biostable 1500 and bioabsorbable ring segments 1510 and bioabsorbable polymer connectors 1000.

EXAMPLES

Example 1

A 99.99% pure magnesium rod of 20 cm length and 5 mm diameter may be directionally solidified from the melt in an induction-heated graphite mold equipped with means for rapid cooling from a single end, e.g., the Easyheat 0112 system available from Ameritherm, based in Scottsville, N.Y. A center section of the rod may be mechanically reduced to a diameter of 1.5 mm, and the rod may then be drawn at an elevated temperature to a wire diameter of 125 microns. The wire may be cut to length, and bent on a wire forming machine into a sinusoidal geometry with a peak-to-valley height of 1.25 mm. A 6 crown ring may be formed by bending a cut length of the linear wire form around a circular mandrel, clamping it in place with opposing wire ends coming in direct contact and overlapped, followed by laser welding to form a lap joint. The metal stent rings may then be electro-polished to a final wire diameter of 120 microns while smoothing weld joints. A series of 12 rings may be welded together at 3 locations per ring to form a 15 mm long vascular stent. The stent platform may be spray coated with 200 microgram coating weight (dry) of D,L PLA-Paclitaxel with a 5% drug load, predominantly on the external or abluminal surface. The drug coated stent may be crimped on an angioplasty balloon catheter, and sterilized by e-beam sterilization.

Example 2

A metal including, e.g., 100% magnesium may be continuously cast by the Ohno continuous casting process used for preparing single crystal fine copper wire, and then drawn to a final diameter of 110 microns, with a length of several miles. The wire may be cut to length sufficient to define one discrete ring, and bent on a wire forming machine into a sinusoidal geometry with a peak to valley height of 1.0 mm. A 6 crown ring may be formed by bending a cut length of the linear wire form around a circular mandrel, clamping it in place with opposing wire ends coming in direct contact and overlapped, followed by laser welding to form a lap joint. The metal stent rings may then be electro-polished to a final wire diameter of 100 microns while smoothing weld joints. Then a stable and dense MgO layer of approximately 1 micron may be formed through electrochemical techniques to passivate the implant surface. A series of 15 rings may be interconnected with filaments of absorbable co-polymer of 10% lactide-90% glycolide to form a vascular stent. The stent platform may be spray coated with 200 microgram coating weight (dry) of D,L PLA-Paclitaxel with a 7.5% drug load. The drug coated stent may be crimped on an angioplasty balloon catheter, and sterilized by ethylene oxide sterilization.

Example 3

A ligating clip may be made from 1.5 mm×1.5 mm square stock a magnesium-based directionally solidified alloy. The square blank may be cast in a heated tool that is equipped for super cooling from one end, resulting in a microstructure of columnar grains extending for its entire length. The square blank may be cut to length, electro-polished, and then passivated with the formation of dense MgO layer. The blank may be formed into an open "V" clip by hot working to form the hinge point, and cold coining of the outer surfaces to form details for engagement and retention within the jaws of a clip applier. The cartridge of clips may be packaged and sterilized by conventional gamma sterilization at a minimum dose of 3.0 MRads. The clips may retain integrity for 4 weeks in vivo, and may be used for small vascular vessel ligation, or for reproductive sterilization.

Example 4

A bone fixation device may be made from a high purity alloy of 98% Mg-2% Ca that is directionally solidified into a 2.5 mm cylindrical blank, which is subsequently tapered in a secondary grinding process. The pin may then be electro-polished to remove surface contaminants and then treated by electrochemical means to form a dense magnesium oxide layer. The pin preferably possesses the necessary mechanical strength and ductility for an interference fit for insertion into a pre-drilled hole in two bone fragments. The pin preferably retains physical integrity and prevents micro-motion between the fragments for period of 12 weeks, and is subsequently fully absorbed.

Example 5

A directionally solidified wire of pure Mg with 10-90 PLGA filament longitudinal connectors and spray coated paclitaxel-PLA coating may be made as follows. High purity magnesium may be directionally solidified and drawn into a 125 micron diameter round wire. The wire may have an ultimate tensile strength of 125 MPa and elongation to break greater than 25%. The wire may be formed on a four slide wire forming machine into conventional sinusoidal or racetrack geometry with a ring height of 1.0 mm in the crimped state. A 6 crown ring may be formed by bending the linear wire form around a circular mandrel, clamping it place with opposing wire ends coming in direct contact and overlapped, followed by laser welding to form a lap joint. The metal stent rings may then electropolished to a final wire diameter of 120 microns while smoothing weld joints. Longitudinal connectors may be made from 10-90 PLGA, by taking 12 rings and lacing or weaving them together axially with 3 filament bundles, each equivalent to 5-0 Vicryl suture, and spaced at approximately 120 degrees apart around the ring circumference. The final composite assembly may be heat set at 60° C. to a final length of 15 mm. The assembly may be spray coated with 200 microgram coating weight (dry) of D,L PLA-Paclitaxel with a 5% drug load, predominantly on the external or abluminal surface. The drug-coated stent may be crimped on an angioplasty balloon catheter, and sterilized by e-beam sterilization.

Example 6

A magnesium alloy laser-cut ring with extruded tubular 5050 PLGA polymer longitudinal connectors and a coating of 8020 PLGA polymer with 10% paclitaxel may be made as follows. A magnesium alloy may be formed into a 2.0 mm (outside diameter) hypo-tube. The hypo-tube may be laser cut into ring segments, with 8 crowns per ring. Each ring segment may have at least 2 elongated stud features of 0.4 mm length and facing matching studs on an opposing ring. The rings may then be connected by flexible longitudinal connectors of 1.0 mm long tubular extrusions of 50-50 PLGA placed over each stud. Fourteen rings with 13 sets of connectors may be assembled into a 20 mm stent, expandable to 3.0 mm diameter. The assembly may be spray coated with a 250 microgram coating weight (dry) of 8020 PLGA polymer pre-compounded with 10% (by weight) Paclitaxel drug. The drug coated stent may be crimped on an angioplasty balloon catheter and sterilized by e-beam.

Example 7

Hyper-fine grain, Mg—Ca alloy wire with Polydioxanone polymer longitudinal connectors and a D,L-PLA-Sirolimus Drug Coating may be made as follows. High purity magnesium-1% Ca with grain size below 5 microns may be drawn and annealed into a 100 micron wire. The wire may be formed into a 6 crown design and welded into a ring. Twelve rings may be equally spaced in a cavity of a steel mold, and poyldioxanone (PDO) in a solvent solution may be vacuum injected into the cavity. Following secondary processes for solvent removal and annealing, the structure may be 15 mm long with 12 metal ring segments. The assembly may be spray coated with 200 microgram coating weight (dry) comprised of 50% D,L PLA and 50% Sirolimus.

Example 8

A Mg-alloy wire-PGA fiber braid with high load chemoactive agent was made as follows. An alloy of magnesium was melted and processed into 160 micron wire. The wire was formed into continuous sinusoid wave form and then wrapped in a helical geometry around a 4.0 mm cylindrical mandrel. The tubular helical structure rings were coupled by longitudinal polymer connectors of Vicryl 6-0 suture (available from Ethicon Inc. of Somerville N.J.). The finished tubular stent-like implant was 12 mm long and was coated with 120 micrograms (dry weight) of a 95% PLA-5% paclitaxel formulation with a manual pipette system. Following mounting on a balloon catheter and ethylene oxide sterilization, the device was used as a short term, luminal drug delivery platform for treatment of cancer of the esophagus.

Example 9

A 15 mm×3.5 mm diameter coronary stent may include 3 cylindrical or ring segments connected by longitudinal absorbable polymer element s. The proximal and distal ring segment may be made from a 75 micron 316L stainless steel alloy wire that is formed into a sinusoidal waveform that is wrapped around a mandrel and welded to form a segment of 2.5 mm in length. The central ring segment may be formed from a Mg high purity alloy that is cast and drawn into a wire of 100 microns in diameter. The Mg wire may be formed on a multi-slide machine into a continuous sinusoidal waveform, wound on a mandrel, and laser welded at select connection points between subsequent rows of rings to form a segment of 8.0 mm in length. The three segments may be connected by interlacings of a 6-0 Vicryl absorbable PLGA suture, with an effective connector length of 0.5 mm each. The total length may equal 2.5+0.5+9+0.5+2.5=15 mm. The entire assembly may be coated with a formulation of approximately 6% Paclitaxel in 90-10 PLGA, crimped on an angioplasty catheter, packaged, and sterilized.

Example 10

A 20 mm×3.5 mm diameter coronary stent may include 3 cylindrical or ring segments connected by longitudinal absorbable polymer elements. The proximal and distal ring segments may be made by laser cutting a cobalt chrome hypo tube into an open cell stent geometry followed by electropolishing down to an 80 micron strut thickness. The effective length when expanded may be 4 mm, and the design may include eyelet features to facilitate interlacing with adjacent segments. The central segment may be made of mono-crystalline magnesium wire that is formed into a continuous sinusoidal waveform that is wrapped on a cylindrical mandrel and laser welded at given intervals to form a flexible segment 12 mm in length. The proximal, central and distal rings may be connected in a similar manner by interlacing with 6-0 PDO absorbable monofilament sutures to form an intraluminal implant of about 20 mm in length. The entire assembly may be coated with a 50-50 formulation of Sirolimus and DL-PLA with approximately 10 micrograms drug per stent mm in length. The stent assembly may be crimped on an angioplasty balloon catheter, packaged and sterilized.

Example 11

A 30 mm×3.0 mm balloon expandable stent may be produced by means similar to the examples described as Example 10, with the exception of a third biostable segment at the center of the assembly. The stent may possess a proximal cobalt chrome laser cut segment of 4 mm, a magnesium wire form segment of 10 mm, a center cobalt chrome segment of 2 mm, another 10 mm magnesium segment, and the distal cobalt chrome ring segment of 4 mm, all interlaced together with 6-0 PDS absorbable monofilament suture. The entire assembly may be coated with a formulation of approximately 6% PT' x in 90-10 PLGA, crimped on an angioplasty catheter, packaged, and sterilized.

Those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described. Various materials, geometries, sizes, and interrelationships of elements may be practiced in various combinations and permutations, and all such variants and equivalents are to be considered part of the invention.

What is claimed is:

1. A bioabsorbable implant comprising:
a directionally solidified and elongated metallic element comprising more than about 80% by weight a metal selected from the group consisting of magnesium, iron, zinc, and manganese, and combinations thereof and being substantially free of rare earth metals, the elongated metallic element defining at least a portion of the bioabsorbable implant,
wherein the metal defines at least one of (i) a continuous single grain having an aspect ratio of grain length to grain diameter of at least 10:1 and (ii) a columnar microstructure including one or more columnar grains extending substantially the entire length of the implant, the one or more columnar grains each having an average grain length of at least about 1 mm and an average grain diameter of less than about 0.2 mm; and
wherein the metal is configured to exhibit enhanced strength and physical integrity post-implantation by being substantially free of grain boundaries containing impurities.

2. The bioabsorbable implant of claim 1, wherein the one or more columnar grains each have an an aspect ratio of grain length to grain diameter of at least 10:1.

3. The bioabsorbable implant of claim 1, wherein the one or more columnar grains each have at least one of an average grain length of at least about 10 mm and an average grain diameter of less than about 3 mm.

4. The bioabsorbable implant of claim 1, wherein the elongated metallic element comprises at least one of a wire, rod, and a hollow tube.

5. The bioabsorbable implant of claim 4, wherein the elongated metallic element comprises a wire having a diameter of less than about 0.2 mm.

6. The bioabsorbable implant of claim 1, wherein the bioabsorbable implant is selected from the group consisting of an intraluminal device, a ligating clip, a ligating clip component, a bone fixation device, and a bone-to-soft-tissue fixation device.

7. The bioabsorbable implant of claim 6, wherein the bioabsorbable implant is a bone fixation device selected from the group consisting of a plate, a pin, and a screw.

8. The bioabsorbable implant of claim 6, wherein the bioabsorbable implant is a bone-to-soft-tissue fixation device selected from the group consisting of a suture anchor, an interference screw, and a cross pin.

9. The bioabsorbable implant of claim 1, wherein the elongated metallic element comprises <0.1 weight percent of rare earth metals.

10. A bioabsorbable implant comprising:
   a directionally solidified and elongated metallic element substantially free of rare earth metals and comprising more than 50% by weight a metal selected from the group consisting of magnesium, iron, zinc, manganese and combinations thereof, the elongated metallic element defining at least a portion of the bioabsorbable implant and comprising a wire defining at least one of a continuous single grain and a columnar microstructure including one or more columnar grains extending substantially the entire length of the implant, the wire exhibiting enhanced strength and physical integrity post-implantation by being substantially free of grain boundaries containing impurities, the wire also being formed into at least one of a bioabsorbable continuous helical sinusoid and a first bioabsorbable expandable metal ring and a second bioabsorbable expandable metal ring.

11. A bioabsorbable implant of claim 10, further comprising:
   at least one flexible longitudinal connecter comprising an absorbable polymer, the at least one flexible longitudinal connector being configured to connect the first and second expandable metal rings; and
   a coating comprising a pharmaceutically active agent disposed over at least a portion of at least one of the first and second metal rings and the longitudinal connector.

12. The bioabsorbable implant of claim 11, wherein at least one of the expandable metal rings comprises a stud configured for coupling with an adjacent feature.

13. The bioabsorbable implant of claim 11, wherein at least one of the expandable rings forms an aperture adapted for coupling with the at least one flexible longitudinal connector.

14. The bioabsorbable implant of claim 11, wherein at least one flexible longitudinal connector comprises at least one of a biodegradable homopolymer and a aliphatic polyester selected from the group consisting of lactic acid, lactide, glycolic acid, glycolide, caprolactone, dioxanone, trimethylcarbonate, and co-polymers and blends thereof.

15. The bioabsorbable implant of claim 11, wherein the at least one flexible longitudinal connector comprises at least one of directionally oriented absorbable filaments extending along a length of the bioabsorbable implant and extruded tubes of absorbable polymer.

16. The bioabsorbable implant of claim 11, wherein the pharmaceutically active agent is selected from the group consisting of a potent anti-proliferative to human smooth muscle cells, taxane, an mTOR agent, and a chemoactive agent suitable for cancer treatment.

17. The bioabsorbable implant of claim 10, wherein the continuous single grain has an aspect ratio of grain length to grain diameter of at least 10:1 and the one or more columnar grains each have an aspect ratio of grain length to grain diameter of at least 10:1.

\* \* \* \* \*

UNITED STATES PATENT AND TRADEMARK OFFICE
CERTIFICATE OF CORRECTION

| | | |
|---|---|---|
| PATENT NO. | : 8,888,841 B2 | Page 1 of 1 |
| APPLICATION NO. | : 13/165247 | |
| DATED | : November 18, 2014 | |
| INVENTOR(S) | : Ioannis Pandelidis and Mark Steckel | |

It is certified that error appears in the above-identified patent and that said Letters Patent is hereby corrected as shown below:

In the Claims

Column 16, Claim 2, line 54, please delete the first occurrence of the term "an"

Signed and Sealed this
Fifth Day of May, 2015

Michelle K. Lee
*Director of the United States Patent and Trademark Office*